US011453706B2

(12) United States Patent
Poznansky et al.

(10) Patent No.: US 11,453,706 B2
(45) Date of Patent: Sep. 27, 2022

(54) HSP FUSION PROTEIN WITH ANTI-CHEMOREPELLANT AGENT FOR TREATMENT OF INFECTIOUS DISEASE

(71) Applicant: The General Hospital Corporation, Boston, MA (US)

(72) Inventors: Mark C. Poznansky, Newton Center, MA (US); Jeffrey A. Gelfand, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 16/331,847

(22) PCT Filed: Sep. 8, 2017

(86) PCT No.: PCT/US2017/050630

§ 371 (c)(1),
(2) Date: Mar. 8, 2019

(87) PCT Pub. No.: WO2018/049124

PCT Pub. Date: Mar. 15, 2018

(65) Prior Publication Data

US 2019/0375801 A1 Dec. 12, 2019

Related U.S. Application Data

(60) Provisional application No. 62/385,865, filed on Sep. 9, 2016.

(51) Int. Cl.

| | |
|---|---|
| ***A61K 39/04*** | (2006.01) |
| ***C07K 14/35*** | (2006.01) |
| ***A61P 31/00*** | (2006.01) |
| ***A61K 31/395*** | (2006.01) |
| ***A61K 35/17*** | (2015.01) |
| ***C07K 14/47*** | (2006.01) |
| ***C07K 19/00*** | (2006.01) |
| *A61K 38/00* | (2006.01) |

(52) U.S. Cl.

CPC ............ *C07K 14/35* (2013.01); *A61K 31/395* (2013.01); *A61K 35/17* (2013.01); *A61P 31/00* (2018.01); *C07K 14/4702* (2013.01); *C07K 19/00* (2013.01); *A61K 38/00* (2013.01)

(58) Field of Classification Search

CPC ....................... A61K 39/00; A61K 39/001176; A61K 39/02; A61K 39/395; A61K 39/40

USPC ..... 424/9.1, 9.2, 130.1, 134.1, 159.1, 163.1, 424/178.1, 278.1

See application file for complete search history.

(56) References Cited

U.S. PATENT DOCUMENTS

| | | | | |
|---|---|---|---|---|
| 4,313,927 | A * | 2/1982 | Fridlender | G01N 33/56983 435/5 |
| 5,075,109 | A | 12/1991 | Tice et al. | |
| 5,514,555 | A | 5/1996 | Springer et al. | |
| 5,583,131 | A | 12/1996 | Bridger et al. | |
| 6,322,788 | B1 * | 11/2001 | Kim | C07K 16/1271 424/133.1 |
| 6,448,054 | B1 | 9/2002 | Poznansky et al. | |
| 7,935,692 | B2 | 5/2011 | Bridger et al. | |
| 7,943,133 | B2 | 5/2011 | Gelfand | |
| 8,143,387 | B2 | 3/2012 | Gelfand | |
| 2008/0300165 | A1 * | 12/2008 | Poznansky | A61K 38/19 514/1.1 |
| 2011/0129484 | A1 * | 6/2011 | Gelfand | A61P 37/00 424/178.1 |

FOREIGN PATENT DOCUMENTS

| | | |
|---|---|---|
| WO | WO 2017/1564612 | 9/2017 |
| WO | WO 2018/049124 | 3/2018 |

OTHER PUBLICATIONS

PCT International Preliminary Report on Patentability in International Appln. No. PCT/US2017/50630, dated Mar. 12, 2019, 9 pages.

PCT International Search Report and Written Opinion in International Appln. No. PCT/US2017/50630, dated Nov. 22, 2017, 11 pages.

Santini et al., "A controlled-release microchip," Nature, Jan. 1999, 397(6717):335-338.

Jianping et al., "A novel mycobacterial Hsp70-containing fusion protein targeting mesothelin augments antitumor immunity and prolongs survival in murine models of ovarian cancer and mesothelioma," Journal of Hematology and Oncology, Feb. 2014, 7(15): 14 pages.

* cited by examiner

*Primary Examiner* — Jennifer E Graser

(74) *Attorney, Agent, or Firm* — Fish & Richardson P.C.

(57) ABSTRACT

This disclosure is directed to immune treatment of a disease (e.g., an infectious disease) using a fusion protein in combination with an anti-chemorepellant agent. In particular, the fusion protein comprises an antigen-binding domain (e.g., an antibody or antibody fragment) and a stress protein domain.

14 Claims, No Drawings

HSP FUSION PROTEIN WITH ANTI-CHEMOREPELLANT AGENT FOR TREATMENT OF INFECTIOUS DISEASE

STATEMENT OF PRIORITY

This application is a 35 U.S.C. § 371 national phase application of PCT Application PCT/US2017/050630 filed Sep. 8, 2017, which claims the benefit of U.S. Provisional Application Ser. No. 62/385,865, filed Sep. 9, 2016; the entire contents of each of which are incorporated by reference herein in its entirety.

STATEMENT OF GOVERNMENT SUPPORT

This invention was made with government support. The U.S. Government has certain rights in this invention.

FIELD OF THE INVENTION

This disclosure is directed to immune treatment of a disease (e.g., an infectious disease) using a fusion protein in combination with an anti-chemorepellant agent. In particular, the fusion protein comprises an antigen-binding domain (e.g., an antibody or antibody fragment) and a stress protein domain.

BACKGROUND OF THE INVENTION

Immunotherapy is a promising treatment for infectious diseases as well as other diseases. Immunotherapy treats disease by inducing, enhancing, augmenting, or suppressing an immune response in a patient.

One aspect of immunotherapy seeks to increase the patient's own immune response to disease-associated antigens. For example, U.S. Pat. Nos. 8,143,387 and 7,943,133 describe fusion proteins with an antibody portion fused to a stress protein that are effective at eliciting T cell-mediated immune response.

There is a need for improved immunotherapy to enhance a patient's immune response to infectious diseases and other diseases.

SUMMARY OF THE INVENTION

This invention is directed to immune treatment of a pathogen infection using a fusion protein in combination with an anti-chemorepellant (i.e., an anti-fugetactic) agent. In particular, the fusion protein comprises an antigen-binding domain (e.g., an antibody or antibody fragment) and a stress protein domain.

Stress proteins are very efficient at presenting antigens to antigen-presenting cells and provoking a T cell response. They have been particularly effective at eliciting cell mediated immune and humoral immune responses by this pathway.

The fusion protein binds to antigens with high affinity, is highly immunogenic, exhibits MHC class I priming, provokes a T cell response and is able to be produced in non-mammalian systems such as *E. coli*. The fusion protein is thus suitable for use as a highly immunogenic vaccine for the prevention or treatment of a number of diseases, including infectious, inflammatory, or autoimmune disease. Non-limiting examples of fusion proteins can be found in U.S. Pat. Nos. 8,143,387 and 7,943,133 and PCT Application Number PCT/US2017/021911, each of which is incorporated herein by reference in its entirety.

Pathogen-infected cells may secrete concentrations of chemokines that are sufficient to repel immune cells from the site of pathogen infection, thus creating a "fugetactic wall" or "chemorepellant wall" around the pathogen-infected cells. The chemorepellant wall reduces the immune system's ability to target and eradicate the pathogens. For example, repulsion of pathogen antigen-specific T-cells, e.g., from a pathogen that induces high expression levels of CXCL12 or interleukin 8 (IL-8), allows the pathogens or the pathogen-infected cells to evade immune control. Anti-chemorepellant agents inhibit the chemorepellant activity of pathogens and allow the patient's immune system to target the pathogens and/or the pathogen-infected cells. Anti-chemorepellant agents and the systemic delivery of anti-chemorepellant agents are known in the art (see, for example, U.S. Patent Application Publication No. 2008/0300165, incorporated herein by reference in its entirety).

Without being bound by theory, it is believed that the antigen-binding domain of the fusion protein will bind to the target (e.g., pathogen), and the stress protein domain will induce maturation of antigen-presenting cells (e.g., dendritic cells), resulting in a T cell response to the target. In combination, the anti-chemorepellant agent will inhibit the chemorepellant activity of the target with regard to the immature antigen-presenting cells and/or T-cells, such that the immune cells are able to penetrate the "chemorepellant wall" and access the target. In some embodiments, the combination results in additive or synergistic effects.

In one embodiment, this invention relates to a method for treating a disease caused by a pathogen in a patient wherein the pathogen or the pathogen-infected cell expresses chemorepellant properties, the method comprising a) administering to the patient an effective amount of a fusion protein and b) concurrently administering to the patient an effective amount of an anti-chemorepellant agent; wherein the combination of the fusion protein and the anti-chemorepellant agent treat the disease. In one embodiment, the fusion protein comprises a target binding component and a stress protein component, wherein the target binding component binds to the pathogen and/or a cell infected by the pathogen, and the stress protein component activates dendritic cells, leading to the generation of CD3 positive T-cells that target antigens associated with the pathogen and/or the pathogen-infected cells In one embodiment, the pathogen is a virus, a bacterium, a parasite, a fungus, or other microorganism.

Anti-chemorepellant agents may include, without limitation, molecules that inhibit expression of CXCL12 or CXCR4 or CXCR7 (e.g., antisense or siRNA molecules), molecules that bind to CXCL12 or CXCR4 or CXCR7 and inhibit their function (e.g., antibodies or aptamers), molecules that inhibit dimerization of CXCL12 or CXCR4 or CXCR7, and antagonists of CXCR4 or CXCR7. In one embodiment, the inhibitor of CXCL12 signaling is a CXCR4 antagonist. In one embodiment, the anti-chemorepellant agent is AMD3100 or a derivative thereof, AMD11070 (also called AMD070), AMD12118, AMD11814, AMD13073, FAMD3465, C131, BKT140, CTCE-9908, KRH-2731, TC14012, KRH-3955, BMS-936564/MDX-1338, LY2510924, GSK812397, KRH-1636, T-20, T-22, T-140, TE-14011, T-14012, TN14003, TAK-779, AK602, SCH-351125, tannic acid, NSC 651016, thalidomide, GF 109230X, an antibody that interferes with dimerization of a chemorepellant chemokine, such as CXCL12, or an antibody that interferes with dimerization of a receptor for a chemorepellant chemokine, such as CXCR4 or CXCR7. In one embodiment, the anti-chemorepellant agent is AMD3100 (1,1'-[1,4-phenylenebis(methylene)]bis

[1,4,8,11-tetraazacyclotetradecane]; plerixafor). AMD3100 is described in U.S. Pat. No. 5,583,131, which is incorporated by reference herein in its entirety. In one embodiment, the anti-chemorepellant agent is a CXCR7 antagonist. The CXCR7 antagonist can be but is not limited to CCX771, CCX754, or an antibody that interferes with the dimerization of CXCR7. In certain embodiments, the anti-chemorepellant agent is not an antibody. In certain embodiments, the anti-chemorepellant agent is not a heparinoid. In certain embodiments, the anti-chemorepellant agent is not a peptide.

In one embodiment, the anti-chemorepellant agent and the fusion protein are co-administered. In one embodiment, the anti-chemorepellant agent is administered prior to administration of the fusion protein. In one embodiment, the anti-chemorepellant agent is administered after administration of the fusion protein.

In one aspect, the stress protein component comprises a heat shock protein or fragments and/or modified sequences thereof. In one embodiment, the heat shock protein is HSP70 or an immune activating fragment and/or modified sequence thereof. In one embodiment, the HSP70 or the immune activating fragment and/or modified sequence thereof is from *Mycobacterium tuberculosis.*

The pathogen binding component may be any antibody or other molecule that recognizes a pathogen of interest. In one aspect, the pathogen binding component is a single chain antibody. In one aspect, the pathogen binding component is a variable domain fragment. In one aspect, the pathogen binding component is a Fab portion of an antibody.

In one aspect, the pathogen binding component is specific for a pathogen antigen (e.g., a pathogen-specific antigen or a pathogen-associated antigen). The pathogen antigen may be any identifiable cell surface antigen that is expressed by a pathogen of interest or by a cell infected with the pathogen. In one embodiment, the pathogen antigens include, but are not limited to, surface polysaccharide antigens, secreted toxins or other secreted antigens, or any surface antigen produced by the pathogen or infected cells.

The methods and compositions described herein may be used to treat any pathogen infection. More preferably, the pathogenic infection exhibits a chemorepellant effect. In one embodiment, the chemorepellant effect is mediated by overexpression of CXCL12 or other chemorepellant chemokine by the pathogen or pathogen-infected cells. In one embodiment, the method further comprises selecting a patient having an infection that exhibits a chemorepellant effect.

In one embodiment, the term "pathogen" refers to a pathogen sample, including but not limited to intact pathogens, viable pathogens, non-viable pathogens, viable or non-viable cells infected by a pathogen or pathogens, pathogen-specific antigens (e.g., isolated antigen, partially isolated antigen, recombinant antigen, etc.), and/or other materials derived from pathogens or pathogen-infected cells.

In one embodiment, the pathogen comprises a virus, a bacterium, a fungus, or a parasite, or other microorganism.

Viral causes of infectious human diseases (and their associated diseases) that can be treated by the composition, compounds and methods described herein include, but are not limited to, Influenza A virus (including 'swine flu' such as the 2009 H1N1 strain); Influenza B-C virus (coryza; 'common cold'); Human adenovirus A-C(various respiratory tract infections; pneumonia); Human Para-influenza virus (coryza; 'common cold;' croup); Mumps virus (epidemic parotitis); Rubeola virus (measles); Rubella virus (German measles); Human respiratory syncytial virus (RSV) (coryza; 'common cold'); Human coronavirus (SARS virus) (SARS); Human rhinovirus A-B (coryza; 'common cold'); parvovirus B19 (fifth disease); variola virus (smallpox); varicella-zoster virus (herpes virus) (chickenpox); Human enterovirus (coryza; 'common cold'); *Bordetella pertussis* (whooping cough); *Neisseria meningitidis* (meningitis); *Corynebacterium diphtherias* (diphtheria); *Mycoplasma pneumoniae* (pneumonia); *Mycobacterium tuberculosis* (tuberculosis); *Streptococcus pyogenes/pneumoniae* (strep throat, meningitis, pneumonia); and *Haemophilus influenza Type B* (epiglottis, meningitis, pneumonia).

In one embodiment, the virus comprises Adeno-associated virus, Aichi virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus, Chandipura virus, Chikungunya virus, Cosavirus A, Cowpox virus, Coxsackievirus, Crimean-Congo hemorrhagic fever virus, Dengue virus, Dhori virus, Dugbe virus, Duvenhage virus, Eastern equine encephalitis virus, Ebola virus, Echovirus, Encephalomyocarditis virus, Epstein-Barr virus, European bat lyssavirus, GB virus C/Hepatitis G virus, Hantaan virus, Hendra virus, Hepatitis A virus, Hepatitis B virus, Hepatitis C virus, Hepatitis E virus, Hepatitis delta virus, Herpes simplex virus, Herpes zoster virus, Horsepox virus, Human adenovirus, Human astrovirus, Human coronavirus, Human cytomegalovirus, Human enterovirus 68, 70, Human herpesvirus 1, Human herpesvirus 2, Human herpesvirus 6, Human herpesvirus 7, Human herpesvirus 8, Human immunodeficiency virus, Human papillomavirus 1, Human papillomavirus 2, Human papillomavirus 16, 18, Human parainfluenza, Human parvovirus B19, Human respiratory syncytial virus, Human rhinovirus, Human SARS coronavirus, Human spumaretrovirus, Human T-lymphotropic virus, Human torovirus, Influenza A virus, Influenza B virus, Influenza C virus, Isfahan virus, JC polyomavirus, Japanese encephalitis virus, Junin arenavirus, KI Polyomavirus, Kunjin virus, Lagos bat virus, Lake Victoria marburgvirus, Langat virus, Lassa virus, Lordsdale virus, Louping ill virus, Lymphocytic choriomeningitis virus, Machupo virus, Mayaro virus, MERS coronavirus, Measles virus, Mengo encephalomyocarditis virus, Merkel cell polyomavirus, Mokola virus, Molluscum contagiosum virus, Monkeypox virus, Mononucleosis virus, Mumps virus, Murray valley encephalitis virus, New York virus, Nipah virus, Norwalk virus, O'nyong-nyong virus, Orf virus, Oropouche virus, Pichinde virus, Poliovirus, Punta toro phlebovirus, Puumala virus, Rabies virus, Rift valley fever virus, Rosavirus A, Ross river virus, Rotavirus A, Rotavirus B, Rotavirus C, Rubella virus, Sagiyama virus, Salivirus A, Sandfly fever sicilian virus, Sapporo virus, SARS virus, Semliki forest virus, Seoul virus, Simian foamy virus, Simian virus 5, Sindbis virus, Southampton virus, St. Louis encephalitis virus, Tick-borne powassan virus, Torque teno virus, Toscana virus, Uukuniemi virus, Vaccinia virus, Varicella-zoster virus, Variola virus, Venezuelan equine encephalitis virus, Vesicular stomatitis virus, Western equine encephalitis virus, WU polyomavirus, West Nile virus, Yaba monkey tumor virus, Yaba-like disease virus, Yellow fever virus, Zika virus or synthetic viruses.

In another embodiment, the bacterium comprises *Acetobacter aurantius, Acinetobacter baumannii, Actinomyces israelii, Agrobacterium radiobacter, Agrobacterium tumefaciens, Anaplasma, Anaplasma phagocytophilum, Azorhizobium caulinodans, Azotobacter vinelandii, Bacillus anthracis, Bacillusbrevis, Bacillus cereus, Bacillus fusiformis, Bacillus licheniformis, Bacillus megaterium, Bacillus*

*mycoides, Bacillus stearothermophilus, Bacillus subtilis, Bacteroides fragilis, Bacteroides gingivalis, Bacteroides melaninogenicus* (aka *Prevotella melaninogenica*), *Bartonella henselae, Bartonella quintana, Bordetella, Bordetella bronchiseptica, Bordetella pertussis, Borrelia burgdorferi, Brucella, Brucella abortus, Brucella melitensis, Brucella suis, Burkholderia, Burkholderia mallei, Burkholderia pseudomallei, Burkholderia cepacia, Calymmatobacterium granulomatis, Campylobacter, Campylobacter coli, Campylobacter fetus, Campylobacter jejuni, Campylobacter pylori, Chlamydia, Chlamydia trachomatis, Chlamydophila, Chlamydophila pneumoniae* (aka *Chlamydia pneumoniae*), *Chlamydophila psittaci* (aka *Chlamydia psittaci*), *Clostridium, Clostridium botulinum, Clostridium difficile, Clostridium perfringens* (aka *Clostridium* welchii), *Clostridium tetani, Corynebacterium, Corynebacterium diphtheria, Corynebacterium fusiforme, Coxiella burnetii, Ehrlichia chaffeensis, Enterobacter cloacae, Enterococcus, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus, Haemophilus ducreyi, Haemophilus influenza, Haemophilus parainfluenzae, Haemophilus pertussis, Haemophilus vaginalis, Helicobacter pylori, Klebsiella pneumonia, Lactobacillus, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium, Mycobacterium avium, Mycobacterium bovis, Mycobacterium diphtheria, Mycobacterium intracellulare, Mycobacterium leprae, Mycobacterium lepraemurium, Mycobacterium phlei, Mycobacterium smegmatis, Mycobacterium tuberculosis, Mycoplasma, Mycoplasma fermentans, Mycoplasma genitalium, Mycoplasma hominis, Mycoplasma penetrans, Mycoplasma pneumonia, Neisseria, Neisseria gonorrhoeae, Neisseria meningitides, Pasteurella, Pasteurella multocida, Pasteurella tularensis, Peptostreptococcus, Porphyromonas gingivalis, Prevotella melaninogenica*(aka *Bacteroides melaninogenicus*), *Pseudomonas aeruginosa, Rhizobium radiobacter, Rickettsia, Rickettsia prowazekii, Rickettsia psittaci, Rickettsia Quintana, Rickettsia rickettsii, Rickettsia trachomae, Rochalimaea, Rochalimaea henselae, Rochalimaea Quintana, Rothia dentocariosa, Salmonella, Salmonella enteritidis, Salmonella typhi, Salmonella typhimurium, Serratia marcescens, Shigella dysenteriae, Staphylococcus, Staphylococcus aureus, Staphylococcus epidermidis, Stenotrophomonas maltophilia, Streptococcus, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumonia, Streptococcus pyogenes, Streptococcus rattus, Streptococcus salivarius, Streptococcus sanguis, Streptococcus sobrinus, Treponema, Treponema pallidum, Treponema denticola, Vibrio, Vibrio cholera, Vibrio comma, Vibrio parahaemolyticus, Vibrio vulnificus, Wolbachia, Yersinia, Yersinia enterocolitica, Yersinia pestis*, or *Yersinia pseudotuberculosis*.

In a further embodiment, the fungus comprises *Acremonium; Absidia* (e.g., *Absidia corymbifera*, etc.); *Aspergillus* (e.g., *Aspergillus clavatus, Aspergillus flavus, Aspergillus fumigatus, Aspergillus nidulans, Aspergillus niger, Aspergillus terreus, Aspergillus verslcolor*, etc.); *Blastomyces* (e.g., *Blastomyces dermatitidis*, etc.); *Candida* (e.g., *Candida albicans, Candida glabrata, Candida guilliermondii, Candida kefyr, Candida krusei, Candida parapsilosis, Candida stellatoidea, Candida tropicalis, Candida utilis*, etc.); *Cladosporium* (e.g., *Cladosporivm trichoides*, etc.); *Coccidioides* (e.g., *Coccidioides immitis*, etc.); *Cryptococcus* (e.g., *Cryptococcus neoformans*, etc.); *Cunninghamella* (e.g., *Cunninghamella elegans*, etc.); *Dermatophyte; Exophiala* (e.g., *Exophiala dermatitidis, Exophiala spinifera*, etc.); *Epidermophyton* (e.g., *Epidermophyton floccosum*, etc.); *Fonsecaea* (e.g., *Fonsecaea pedrosoi*, etc.); *Fusarium* (e.g., *Fusarium solani*, etc.); Geotrichu (e.g., *Geotrichum candiddum*, etc.); *Histoplasma* (e.g., *Histoplasma capsulatum* var. *capsulatum*, etc.); *Malassezia* (e.g., *Malassezia furfur*, etc.); *Microsporum* (e.g., *Microsporum canis, Microsporum gypseum*, etc.); *Mucor; Paracoccidioides* (e.g., *Paracoccidioides brasiliensis*, etc.); *Penicillium* (e.g., *Penicillium arneffei*, etc.); *Phialophora; Pneumocystis* (e.g., *Pneumocystis carinii*, etc.); *Pseudallescheria* (e.g., *Pseudallescheria boydii*, etc.); *Rhizopus* (e.g., *Rhizopus microsporus* var. *rhizopodiformis, Rhizopus oryzae*, etc.); *Saccharomyces* (e.g., *Saccharomyces cerevisiae*, etc.); *Scopulariopsis; Sporothrix* (e.g., *Sporothrix schenckii*, etc.); *Trichophyton* (e.g., *Trichophyton mentagrophytes, Trichophyton rubru*, etc.); or *Trichosporon* (e.g., *Trichosporon asahii, Trichosporon cutaneum*, etc.).

In one embodiment, the fusion protein is administered via injection. In one embodiment, the fusion protein is injected directly into the pathogen-infected cells. In one embodiment, the fusion protein is injected into a pathogen-infected area or proximal to the area. In one embodiment, the fusion protein is systemically administered.

In one embodiment, the anti-chemorepellant agent is administered via injection. In one embodiment, the anti-chemorepellant agent is administered directly to the infected region or proximal to the region. In one embodiment, the anti-chemorepellant agent is administered systemically.

In one aspect, this invention relates to a pharmaceutical composition comprising a fusion protein and an anti-chemorepellant agent. In one embodiment, the composition further comprises antigen-presenting cells. In one embodiment, the antigen-presenting cells are dendritic cells.

DETAILED DESCRIPTION

After reading this description, it will become apparent to one skilled in the art how to implement the invention in various alternative embodiments and alternative applications. However, not all embodiments of the present invention are described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

Definitions

Unless defined otherwise, all technical and scientific terms used herein have the same meaning as commonly understood by one of ordinary skill in the art to which this invention belongs.

In this specification and in the claims that follow, reference will be made to a number of terms that shall be defined to have the following meanings:

The terminology used herein is for the purpose of describing particular embodiments only and is not intended to be limiting of the invention. As used herein, the singular forms "a," "an," and "the" are intended to include the plural forms as well, unless the context clearly indicates otherwise.

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the reagents described herein are merely exemplary and that equivalents of such are known in the art.

"Optional" or "optionally" means that the subsequently described event or circumstance can or cannot occur, and that the description includes instances where the event or circumstance occurs and instances where it does not.

The term "comprising" or "comprises" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

The term "human pathogen" comprises bacteria, fungi, protozoa, parasites, and viruses, as well as other microorganisms that cause human diseases.

The terms "patient," "subject," "individual," and the like are used interchangeably herein, and refer to any animal, or cells thereof whether in vitro or in situ, amenable to the methods described herein. In one embodiment, the patient, subject, or individual is a mammal. In some embodiments, the mammal is a mouse, a rat, a guinea pig, a non-human primate, a dog, a cat, or a domesticated animal (e.g., horse, cow, pig, goat, sheep). In some embodiments, the patient, subject or individual is a human.

The term "treating" or "treatment" covers the treatment of a disease or disorder described herein, in a subject, such as a human, and includes: (i) inhibiting a disease or disorder, i.e., arresting its development; (ii) relieving a disease or disorder, i.e., causing regression of the disease or disorder; (iii) slowing progression of the disease or disorder; and/or (iv) inhibiting, relieving, or slowing progression of one or more symptoms of the disease or disorder. For example, treatment of infectious diseases or a pathogen includes, but is not limited to, reduction in pathogen-infected cells, elimination of the pathogen and/or pathogen-infected cells, remission of the infection, inhibition of the spread of infectious diseases, reduction or elimination of at least one symptom of the infectious disease, and the like.

The term "administering" or "administration" of an agent to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

"Pharmaceutically acceptable composition" refers to a composition that is suitable for administration to a mammal, particularly, a human.

It is also to be appreciated that the various modes of treatment or prevention of medical diseases and conditions as described are intended to mean "substantial," which includes total but also less than total treatment or prevention, and wherein some biologically or medically relevant result is achieved.

The phrase "concurrently administering" refers to administration of at least two agents to a patient over a period of time. As used herein, the word "concurrently" means sufficiently close in time to produce a combined effect (that is, concurrently can be simultaneously, or it can be two or more events occurring within a short time period before or after each other). Concurrent administration includes, without limitation, separate, sequential, and simultaneous administration.

The term "separate" administration refers to an administration of at least two active ingredients at the same time or substantially the same time by different routes or in different compositions.

The term "sequential" administration refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients.

The term "simultaneous" administration refers to the administration of at least two active ingredients by the same route and at the same time or at substantially the same time.

The term "therapeutic" as used herein means a treatment. A therapeutic effect is obtained by suppression, remission, or eradication of a disease state.

The term "prevent" or "preventative" as used herein means a prophylactic treatment. A preventative effect is obtained by delaying the onset of a disease state or decreasing the severity of a disease state when it occurs.

The term "therapeutically effective amount," "prophylactically effective amount," or "effective amount" refers to an amount of the agent that, when administered, is sufficient to cause the desired effect. For example, an effective amount of an anti-chemorepellant agent may be an amount sufficient to have an anti-chemorepellant effect on a pathogen or a pathogen-infected cell (e.g., to attenuate a chemorepellant effect from the pathogen or the pathogen-infected cell). The therapeutically effective amount of the agent may vary depending on the pathogen being treated and its severity as well as the age, weight, etc., of the patient to be treated. The skilled artisan will be able to determine appropriate dosages depending on these and other factors. The compositions can also be administered in combination with one or more additional therapeutic compounds. In the methods described herein, the therapeutic compounds may be administered to a subject having one or more signs or symptoms of a disease or disorder.

The term "kill" with respect to a cell/cell population is directed to include any type of manipulation that will lead to the death of that cell/cell population.

"Antibodies" as used herein include polyclonal, monoclonal, single chain, chimeric, humanized and human antibodies, prepared according to conventional methodology.

"CXCR4/CXCL12 antagonist" or "CXCR7/CXCL12 antagonist" refers to a compound that antagonizes CXCL12 binding to CXCR4 and/or CXCR7 or otherwise reduces the chemorepellant effect of CXCL12.

By "chemorepellant activity" or "chemorepellant effect" it is meant the ability of an agent to repel (or chemorepel) a eukaryotic cell with migratory capacity (i.e., a cell that can move away from a repellant stimulus), as well as the chemorepellant effect of a chemokine secreted by a cell, e.g., a pathogen-infected cell. Usually, the chemorepellant effect is present in an area around the cell wherein the concentration of the chemokine is sufficient to provide the chemorepellant effect. Some chemokines, including interleukin 8 and CXCL12, may exert chemorepellant activity at high concentrations (e.g., over about 100 nM), whereas lower concentrations exhibit no chemorepellant effect and may even be chemoattractant.

Accordingly, an agent with chemorepellant activity is a "chemorepellant agent." Such activity can be detected using any of a variety of systems well known in the art (see, e.g., U.S. Pat. No. 5,514,555 and U.S. Patent Application Pub. No. 2008/0300165, each of which is incorporated by reference herein in its entirety). A preferred system for use herein is described in U.S. Pat. No. 6,448,054, which is incorporated herein by reference in its entirety.

The term "anti-chemorepellant effect" refers to the effect of the anti-chemorepellant agent to attenuate or eliminate the chemorepellant effect of the chemokine.

"Immune cells" as used herein are cells of hematopoietic origin that are involved in the specific recognition of antigens. Immune cells include antigen presenting cells (APCs), such as dendritic cells or macrophages, B cells, T cells, etc.

The term "anti-pathogen therapy" or "anti-infectious disease therapy" as used herein refers to traditional infection treatments, including antibiotics, antiviral agents, antifungal agents, anti-parasitic agents, and antimicrobial agents, as well as vaccine therapy.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY).

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

A "fusion protein" or "fusion polypeptide" refers to a hybrid polypeptide which comprises polypeptide portions from at least two different polypeptides. The portions may be from proteins of the same organism, in which case the fusion protein is said to be "intraspecies," "intragenic," etc. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. A first polypeptide may be fused to the N-terminus, the C-terminus, or the N- and C-terminus of a second polypeptide. Furthermore, a first polypeptide may be inserted within the sequence of a second polypeptide.

The term "immunogenic" refers to the ability of a substance to elicit an immune response. An "immunogenic composition" or "immunogenic substance" is a composition or substance which elicits an immune response. An "immune response" refers to the reaction of a subject to the presence of an antigen, which may include at least one of the following: making antibodies, developing immunity, developing hypersensitivity to the antigen, and developing tolerance.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

As used herein, a "stress protein," also known as a "heat shock protein" or "Hsp," is a protein that is encoded by a stress gene, and is therefore typically produced in significantly greater amounts upon the contact or exposure of the stressor to the organism. The term "stress protein" as used herein is intended to include such portions and peptides of a stress protein. A "stress gene," also known as "heat shock gene," as used herein, refers to a gene that is activated or otherwise detectably upregulated due to the contact or exposure of an organism (containing the gene) to a stressor, such as but not limited to heat shock, hypoxia, glucose deprivation, heavy metal salts, inhibitors of energy metabolism and electron transport, and protein denaturants, or to certain benzoquinone ansamycins. Nover, L., Heat Shock Response, CRC Press, Inc., Boca Raton, Fla. (1991). "Stress gene" also includes homologous genes within known stress gene families, such as certain genes within the Hsp70 and Hsp90 stress gene families, even though such homologous genes are not themselves induced by a stressor. Each of the terms stress gene and stress protein as used in the present specification may be inclusive of the other, unless the context indicates otherwise.

The term "vaccine" refers to a substance that elicits an immune response and also confers protective immunity upon a subject.

Anti-Chemorepellant Agents

Many pathogens or pathogen-infected cells have chemorepellant effects, e.g., on immune cells, due to chemokines secreted by the pathogens or pathogen-infected cells. High concentrations of the chemokines secreted by the pathogens or pathogen-infected cells can have chemorepellant effects on cells, whereas lower concentrations do not have such effects or even result in chemoattraction. For example, T-cells are repelled by CXCL12 (SDF-1) by a concentration-dependent and CXCR4 receptor-mediated mechanism.

The anti-chemorepellant agent may be any such agent known in the art, for example an anti-chemorepellant agent as described in U.S. Patent Application Publication No. 2008/0300165, which is hereby incorporated by reference in its entirety.

Anti-chemorepellant agents include any agents that specifically inhibit chemokine and/or chemokine receptor dimerization, thereby blocking the chemorepellant response to a chemorepellant agent. Certain chemokines, including IL-8 and CXCL12, can also serve as chemorepellants at high concentrations (e.g., above 100 nM) where much of the chemokine exists as a dimer. Dimerization of the chemokine elicits a differential response in cells, causing dimerization of chemokine receptors, an activity which is interpreted as a chemorepellant signal. Blocking the chemorepellant effect of high concentrations of a chemokine secreted by pathogen-infected cells can be accomplished, for example, by anti-chemorepellant agents which inhibit chemokine dimer formation or chemokine receptor dimer formation. For example, antibodies that target and block chemokine receptor dimerization, e.g., by interfering with the dimerization domains or ligand binding, can be anti-chemorepellant agents. Anti-chemorepellant agents that act via other mechanisms of action, e.g., that reduce the amount of chemorepellant cytokine secreted by the cells, inhibit dimerization, and/or inhibit binding of the chemokine to a target receptor, are also encompassed by the present invention. Where desired, this effect can be achieved without inhibiting the chemotactic action of monomeric chemokine.

In other embodiments, the anti-chemorepellant agent is a CXCR4 antagonist, CXCR3 antagonist, CXCR4/CXCL12 antagonist, CXCR7/CXCL12 antagonist, or selective PKC inhibitor. Anti-chemorepellant agents may include, without limitation, molecules that inhibit expression of CXCL12 or CXCR4 or CXCR7 (e.g., antisense or siRNA molecules), molecules that bind to CXCL12 or CXCR4 or CXCR7 and inhibit their function (e.g., antibodies or aptamers), molecules that inhibit dimerization of CXCL12 or CXCR4 or CXCR7, and antagonists of CXCR4 or CXCR7.

The CXCR4 antagonist can be but is not limited to AMD3100 (plerixafor) or a derivative thereof, AMD11070 (also called AMD070), AMD12118, AMD11814, AMD13073, FAMD3465, C131, BKT140, CTCE-9908, KRH-2731, TC14012, KRH-3955, BMS-936564/MDX-1338, LY2510924, GSK812397, KRH-1636, T-20, T-22, T-140, TE-14011, T-14012, TN14003, thalidomide, GF 109230X, derivatives thereof, or an antibody that interferes with the dimerization of CXCR4. Additional CXCR4 antagonists are described, for example, in U.S. Patent Pub. No. 2014/0219952 and Debnath et al. *Theranostics,* 2013; 3(1): 47-75, each of which is incorporated herein by reference in its entirety, and include TG-0054 (burixafor), AMD3465, NIBR1816, AMD070, and derivatives thereof.

The CXCR3 antagonist can be but is not limited to TAK-779, AK602, or SCH-351125, or an antibody that interferes with the dimerization of CXCR3.

The CXCR4/CXCL12 antagonist can be but is not limited to tannic acid, NSC 651016, or an antibody that interferes with the dimerization of CXCR4 and/or CXCL12.

The CXCR7/CXCL12 antagonist can be but is not limited to CCX771, CCX754, or an antibody that interferes with the dimerization of CXCR7 and/or CXCL12.

The selective PKC inhibitor can be but is not limited to thalidomide or GF 109230X.

In a preferred embodiment, the anti-chemorepellant agent is AMD3100 (plerixafor). AMD3100 is described in U.S. Pat. No. 5,583,131, which is incorporated by reference herein in its entirety.

In one embodiment, the anti-chemorepellant agent is an AMD3100 derivative. AMD3100 derivatives include, but are not limited to, those found in U.S. Pat. Nos. 7,935,692 and 5,583,131 (USRE42152), each of which is incorporated herein by reference in its entirety.

In certain embodiments, the anti-chemorepellant agent is not an antibody. In certain embodiments, the anti-chemorepellant agent is not a heparinoid. In certain embodiments, the anti-chemorepellant agent is not a peptide.

In one embodiment, the anti-chemorepellant agent is coupled with a molecule that allows targeting of a pathogen or a pathogen-infected cell. In one embodiment, the anti-chemorepellant agent is coupled with (e.g., bound to) an antibody specific for the pathogen or a pathogen-infected cell to be targeted. In one embodiment, the anti-chemorepellant agent coupled to the molecule that allows targeting of the pathogen or a pathogen-infected cell is administered systemically.

In one embodiment, the anti-chemorepellant agent is administered in combination with an additional compound that enhances the anti-chemorepellant activity of the agent. In one embodiment, the additional compound is granulocyte colony stimulating factor (G-CSF). In one embodiment, G-CSF is not administered.

Fusion Protein

This disclosure relates to fusion proteins comprising a stress protein component and a pathogen binding component, and methods of using the same. In particular, this disclosure relates to treating a patient having a disease, e.g. a disease caused by a pathogen, that can be recognized by a fusion protein as described herein. Preferably, the disease expresses a chemorepellant activity such that immune cells are inhibited in the vicinity of the diseased cells or pathogen.

Examples and methods of making fusion proteins contemplated in the present invention are described in U.S. Pat. Nos. 8,143,387 and 7,943,133 and PCT Application Number PCT/US2017/021911, each of which is incorporated herein by reference in its entirety.

Stress Protein Component

The stress protein component (also referred to as the stress protein domain) may comprise any polypeptide sequence that activates APCs. In some embodiments, the polypeptide sequence is derived from a stress protein. However, any APC-activating polypeptide is contemplated.

Any suitable stress protein (heat shock protein (Hsp)) can be used in the fusion polypeptides of the present invention. For example, Hsp60 and/or Hsp70 can be used. Turning to stress proteins generally, cells respond to a stressor (typically heat shock treatment) by increasing the expression of a group of genes commonly referred to as stress, or heat shock, genes. Heat shock treatment involves exposure of cells or organisms to temperatures that are one to several degrees Celsius above the temperature to which the cells are adapted. In coordination with the induction of such genes, the levels of corresponding stress proteins increase in stressed cells.

In bacteria, the predominant stress proteins are proteins with molecular sizes of about 70 and 60 kDa, which are commonly referred to as Hsp70 and Hsp60, respectively. Stress proteins appear to participate in important cellular processes such as protein synthesis, intracellular trafficking, and assembly and disassembly of protein complexes. It appears that the increased amounts of stress proteins synthesized during stress serve primarily to minimize the consequences of induced protein unfolding. Indeed, the preexposure of cells to mildly stressful conditions that induce the synthesis of stress proteins affords protection to the cells from the deleterious effects of a subsequent, more extreme stress.

The major stress proteins appear to be expressed in every organism and tissue type examined so far. Also, it appears that stress proteins represent the most highly conserved group of proteins identified to date. For example, when stress proteins in widely diverse organisms are compared, Hsp90 and Hsp70 exhibit 50% or higher identity at the amino acid level and share many similarities at non-identical positions. Similar or higher levels of homology exist between different members of a particular stress protein family within species.

The stress proteins, particularly Hsp70, Hsp60, Hsp20-30 and Hsp 10, are among the major determinants recognized by the host immune system in the immune response to infection by *Mycobacterium tuberculosis* and *Mycobacterium leprae*. However, individuals, including healthy individuals with no history of mycobacterial infection or autoimmune disease, also carry T cells that recognize both bacterial and human Hsp60 epitopes. This system recognizing stress protein epitopes presumably constitutes an "early defense system" against invading organisms. The system may be maintained by frequent stimulation by bacteria and viruses.

Families of stress genes and proteins for use in the fusion polypeptides are those well known in the art and include, for example, Hsp 100-200, Hsp100, Hsp90, Lon, Hsp70, Hsp60, TF55, Hsp40, FKBPs, cyclophilins, Hsp20-30, ClpP, GrpE, Hsp10, ubiquitin, calnexin, and protein disulfide isomerases. In certain embodiments, the stress protein is Hsp70 or Hsp60. In certain embodiments, the stress protein is a fragment of Hsp70 or Hsp60 and/or a modified sequence of Hsp70 or Hsp60. As use herein, a "modified sequence" of a stress protein such as Hsp70 is a sequence comprising one or more additions, deletion, or substitutions that retains at least 50% of at least one of the biological activity of the stress protein, e.g., the ability to stimulate antigen presenting cells, e.g., at least 50%, 60%, 70%, 80%, or more of the biological activity. In some embodiments, the modified sequence has an enhanced biological activity compared to the wild-type sequence. In some embodiments, the modified sequence is one disclosed in PCT Application No. PCT/US2017/021911, incorporated by reference herein in its entirety.

Hsp100-200 examples include Grp170 (for glucose-regulated protein). Hsp100 examples include mammalian Hsp110, yeast Hsp104, ClpA, ClpB, ClpC, ClpX and ClpY. Hsp90 examples include HtpG in *E. coli*, Hsp83 and Hsc83 in yeast, and Hsp90alpha, Hsp90beta and Grp94 in humans. Hsp70 examples include Hsp72 and Hsc73 from mammalian cells, DnaK from bacteria, particularly mycobacteria such as *Mycobacterium leprae*, *Mycobacterium tuberculosis*, and *Mycobacterium bovis* (such as Bacille-Calmette Guerin, referred to herein as Hsp71), DnaK from *Escherichia coli*, yeast, and other prokaryotes, and BiP and Grp78. Hsp60 examples include Hsp65 from mycobacteria. Bacterial Hsp60 is also commonly known as GroEL, such as the GroEL from *E. coli*. TF55 examples include Tepl, TRiC and thermosome. Hsp40 examples include DnaJ from prokaryotes such as *E. coli* and mycobacteria and HSJ1, HDJ1 and Hsp40. FKBPs examples include FKBP12, FKBP13, FKBP25, and FKBP59, Fpr1 and Nep1. Cyclophilin examples include cyclophilins A, B and C. Hsp10 examples include GroES and Cpn10.

In particular embodiments, the stress proteins of the present invention are obtained from enterobacteria, mycobacteria (particularly *M. leprae, M. tuberculosis, M. vaccae, M. smegmatis* and *M. bovis*), *E. coli*, yeast, *Drosophila*, vertebrates, avians, chickens, mammals, rats, mice, primates, or humans.

In one embodiment, the stress protein comprises *Mycobacterium tuberculosis*-derived heat shock protein 70 (MtbHsp70). MtbHsp70 is well characterized and functions as a potent immune-activating adjuvant. It stimulates monocytes and dendritic cells (DCs) to produce CC-chemokines, which attract antigen processing and presenting macrophages, DCs, and effector T and B cells.

A fusion polypeptide may comprise an amino acid sequence that is at least about 80%, 85%, 90%, 95%, 98%, or 99% identical to a stress protein described herein.

A fusion polypeptide may comprise an amino acid sequence which is a fragment and/or modification of the stress protein as described herein.

Target Binding Component

The target binding component of the fusion protein may be any molecule that specifically binds an antigen associated with the disease to be treated. In certain embodiments, the target binding component is an antibody or a fragment thereof.

In one aspect, the target binding component is a single chain antibody. In one aspect, the target binding component is a variable domain fragment. In one aspect, the target binding component is a Fab portion of an antibody.

In one aspect, the target binding component is specific for a pathogen antigen (e.g., a pathogen-specific antigen or a pathogen-associated antigen), and may be referred to as a pathogen binding component. The pathogen antigen may be any identifiable surface antigen or epitope that is expressed by a pathogen of interest or the pathogen-infected cell. In one embodiment, the pathogen antigens include, but are not limited to, surface polysaccharide antigens, secreted toxins or other secreted antigens, or any surface antigen produced by the pathogen or infected cells.

In one aspect, the target binding component is specific for an antigen associated with a pathogen or a pathogen-infected cell. Suitable pathogens and antigens can be found, for example and without limitation, in U.S. Pat. No. 8,143,387, which is incorporated herein by reference in its entirety.

In one embodiment, the target binding component (e.g., antibody) is specific for an epitope associated with an infectious disease. In one embodiment, the target binding component (e.g., antibody) is specific for an epitope associated with a microbial infection, such as a bacterial infection. In one embodiment, the infectious disease is caused by or related to a pathogen selected from the group consisting of bacteria, fungi, viruses, protozoa, parasites, or other microorganisms. In one embodiment, the target binding component (e.g., antibody) is specific for an epitope associated with the pathogen, such as a bacterium. In one embodiment, the bacterium is a non-bacterial toxin expressing bacterium. In one embodiment, the bacterium is a bacterial toxin expressing bacterium. In one embodiment, the target binding component (e.g., antibody) is specific for an epitope associated with a toxin produced by the pathogen. In one embodiment, the target binding component (e.g., antibody) targets one or more symptoms of the infectious disease.

In one embodiment, the antibodies include, but are not limited to, Palivizumab, Actoxumab, Bezlotoxumab, CR6261, Diridavumab, Edobacomab, Efungumab, Exbivirumab, Felvizumab, Firivumab, Foravirumab, Ibalizumab, Libivirumab, Motavizumab, Obiltoxaximab, Pagibaximab, Panobacumab, Pritoxaximab, PRO 140, VRC01LS, Rafivirumab, Raxibacumab, Regavirumab, Setoxaximab, Sevirumab, Suvizumab, Tefibazumab, Tosatoxumab, Tuvirumab, Urtoxazumab, ado-trastuzumab emtansine, alemtuzumab, bevacizumab, cetuximab, denosumab, dinutuximab, ipilimumab, nivolumab, obinutuzumab, ofatumumab, panitumumab, pembrolizumab, pertuzumab, rituximab, and trastuzumab.

Table 1 depicts a non-limiting list of antibodies approved or in trials for infectious disease targets.

TABLE 1

| Antibodies Antibodies | | | |
|---|---|---|---|
| Biologic | Type | Treatment(s) | Target(s) |
| Palivizumab | Humanized | Respiratory syncytial virus | RSV F protein |
| Actoxumab | Human | *Clostridium difficile* colitis | Exotoxin TcdA |
| Bezlotoxumab | Human | *Clostridium difficile* infection | Exotoxin TcdB |

Table 2 lists a fusion protein for an infectious disease target.

TABLE 2

| Fusion protein Fusion Proteins | | | |
|---|---|---|---|
| Biologic | Description | Treatment(s) | Target(s) |
| N/A | Toll-like receptor 4 with IgG1 Fc | Bacterial sepsis | |

Table 3 lists other antibodies for infectious disease uses.

TABLE 3

| Other antibodies for infectious disease uses Antibodies | | |
|---|---|---|
| Antibody | Type | Proposed Treatment/Target |
| Bezlotoxumab | human | *clostridium difficile* colitis |
| CR6261 | human | infectious disease, influenza A |
| Diridavumab | human | influenza A |
| Edobacomab | mouse | sepsis caused by Gram-negative bacteria |
| Efungumab | human | invasive *Candida* infection |
| Exbivirumab | human | hepatitis B |
| Felvizumab | humanized | respiratory syncytial virus infection |
| Firivumab | human | influenza |
| Foravirumab | human | rabies |
| Ibalizumab | humanized | HIV infection |
| Libivirumab | human | hepatitis B |
| Motavizumab | humanized | respiratory syncytial virus |
| Obiltoxaximab | chimeric | *Bacillus anthracis* spores |
| Pagibaximab | chimeric | sepsis (*Staphylococcus*) |
| Panobacumab | human | *Pseudomonas aeruginosa* infection |
| Pritoxaximab | chimeric | Anti-Shiga toxin 1 B subunit |
| PRO 140 | humanized | HIV infection |
| VRCO1LS | humanized | HIV |
| Rafivirumab | human | rabies |
| Raxibacumab | human | anthrax (prophylaxis and treatment) |
| Regavirumab | human | cytomegalovirus infection |
| Setoxaximab | chimeric | *E. coli* |
| Sevirumab | human | cytomegalovirus infection |
| Suvizumab | humanized | viral infections |
| Tefibazumab | humanized | *Staphylococcus aureus* infection |
| Tosatoxumab | human | Anti-*S. aureus* alpha-toxin |
| Tuvirumab | human | chronic hepatitis B |
| Urtoxazumab | humanized | diarrhea caused by *E. coli* |

Bacterial Toxins

Many bacteria have the ability to produce toxins, which is an underlying mechanism by which bacterial pathogens produce disease. Bacterial toxins include lipopolysaccharides, which are associated with the cell wall of Gram-negative bacteria, and proteins, which are released from bacterial cells and may act at tissue sites removed from the site of bacterial growth. Endotoxins are cell-associated toxins and exotoxins are the extracellular diffusible toxins.

In one embodiment, the target binding component (e.g., antibody) is specific for a bacterial toxin or an epitope associated with the bacterial toxin, including an endotoxin or an exotoxin.

Endotoxins include, but are not limited to, the lipopolysaccharides (LPS) or lipooligosaccharides (LOS) that are located in the outer membrane of Grams-negative bacteria. Endotoxins can be released from growing bacteria or from cells that are lysed as a result of effective host defense mechanisms or by the activities of certain antibiotics.

Endotoxins are part of the outer membrane of the cell wall of Gram-negative bacteria. Endotoxin is invariably associated with Gram-negative bacteria whether the organisms are pathogenic or not. Although the term "endotoxin" is occasionally used to refer to any cell-associated bacterial toxin, in bacteriology it is properly reserved to refer to the lipopolysaccharide complex associated with the outer membrane of Gram-negative pathogens such as *Escherichia coli, Salmonella, Shigella, Pseudomonas, Neisseria, Haemophilus influenzae, Bordetella pertussis* and *Vibrio cholerae.*

Enterotoxins are bacterial exotoxins that have an action upon the intestinal mucosa. They may be produced within the intestine by pathogenic bacteria. Bacterial enterotoxins are potent mucosal immunogens that activate both mucosal and systemic immune responses, and thus are the cause of various diseases, which include food poisoning, common diarrhea, colitis, chronic inflammation and dysentery.

Methods of Treatment

The fusion protein as described herein can be used in combination with an anti-chemorepellant agent to treat a disease which is associated with a chemorepellant effect. The disease may be mediated by a pathogen, such as a virus, a bacterium, a fungus, a parasite, a protozoan, or a micro-organism.

In one aspect, this invention relates to a method for treating a disease caused by a pathogen in a patient wherein the pathogen or cells infected by the pathogen express chemorepellant properties, the method comprising administering to the patient: a) an effective amount of a fusion protein; and b) concurrently administering to the patient an effective amount of an anti-chemorepellant agent; wherein the combination of the fusion protein and the anti-chemorepellant agent treat the disease. In one embodiment, the fusion protein comprises a target binding component and a stress protein component, wherein the target binding component binds to the pathogen and/or cells infected by the pathogen, and the stress protein component activates dendritic cells, leading to the generation of CD3 positive T-cells that target antigens associated with the pathogen and/or pathogen-infected cells. In one embodiment, the pathogen is a virus, a bacterium, a protozoan, a parasite, or a fungus.

In one embodiment, the anti-chemorepellant agent and the fusion protein are administered separately, e.g., by the same or different routes. In one embodiment, the anti-chemorepellant agent and the fusion protein are administered simultaneously, in the same or different compositions, e.g., by the same or different routes. In one embodiment, the anti-chemorepellant agent and the fusion protein are administered sequentially, e.g., by the same or different routes.

In one embodiment, the anti-chemorepellant agent is administered prior to administration of the fusion protein. In one embodiment, the anti-chemorepellant agent is administered after administration of the fusion protein. In one embodiment, the anti-fugetactic agent is administered before, during and/or after administration of the fusion protein.

In some embodiments, the anti-chemorepellant agent is administered between one minute and 24 hours prior to administration of the fusion protein. In some embodiments, the anti-chemorepellant agent is administered 1, 2, 3, 4, 5, 6, or 7 days prior to administration of the fusion protein.

In some embodiments, the anti-chemorepellant agent is administered for a period of time sufficient to reduce or attenuate the chemorepellant effect of the pathogen, e.g., such that the anti-chemorepellant agent has an anti-chemorepellant effect; the fusion protein can then be administered for a period of time during which the chemorepellant effect of the pathogen is reduced or attenuated.

In some embodiments, the anti-chemorepellant agent is administered between one minute and 24 hours after administration of the fusion protein. In some embodiments, the anti-chemorepellant agent is administered 1, 2, 3, 4, 5, 6, or 7 days after administration of the fusion protein.

In one embodiment, the anti-chemorepellant agent and/or fusion protein is administered intravenously, subcutaneously, orally, or intraperitoneally. In one embodiment, the anti-chemorepellant agent is administered proximal to (e.g., near or within the same body cavity as) the pathogen or the pathogen-infected cell or region/tissue. In one embodiment, the anti-chemorepellant agent is administered directly into the pathogen, the pathogen-infected cell, a pathogen-infected region or tissue, or into a blood vessel feeding the pathogen-infected cell, region, or tissue. In one embodiment, the anti-chemorepellant agent is administered systemically. In a further embodiment, the anti-chemorepellant agent is administered by microcatheter, an implanted device, or an implanted dosage form.

In one embodiment, the anti-chemorepellant agent is administered in a continuous manner for a defined period. In another embodiment, anti-chemorepellant agent is administered in a pulsatile manner. For example, the anti-chemorepellant agent may be administered intermittently over a period of time.

In one embodiment, the method further comprises administering tot the patient an effective amount of an anti-pathogen agent that targets the pathogen of interest. The anti-pathogen therapy may be any therapy that targets a pathogen, including but not limited to an antimicrobial agent, an antibiotic, an anti-fungal agent, an anti-parasitic agent, an anti-protozoa agent, an anti-viral agent, and the like.

The methods described herein may be used to treat a pathogen or an infectious disease. In one embodiment, the pathogen exhibits a chemorepellant effect. In one embodiment, the chemorepellant effect is mediated by overexpression of CXCL12 or other chemorepellant chemokine, e.g., expresses an amount of CXCL12 in the microenvironment sufficient to have a chemorepellant effect. In one embodiment, the method comprises selecting a patient having an infectious disease which exhibits a chemorepellant effect, e.g., is determined to express or over-express CXCL12, e.g., a concentration of about 100 nM or higher, e.g., about 100, 150, 200, 250, 300, 350, 400, 450, or 500 nM.

In one embodiment, the method further comprises selecting a patient infected by a pathogen that exhibits a chemorepellant effect. In another embodiment, the invention further comprises administering to the patient an effective amount of an anti-chemorepellant agent. The anti-chemorepellant agent and the fusion protein may be administered separately, simultaneously, and/or sequentially. In another aspect, the anti-chemorepellant agent is administered after the administration of the fusion protein. In another aspect, the anti-chemorepellant agent is administered before and/or during the administration of the fusion protein.

In one aspect, the pathogens can be virus, bacteria, protozoa, parasite, or fungus. In another embodiment, the infectious diseases can be caused by virus, bacteria, protozoa, parasite, or fungus.

In one embodiment, the infectious disease can be caused by bacteria, viruses, fungi, parasites, or other microorganism, e.g., as listed above. The non-limiting list of infectious diseases and their sources that can be treated by the composition, compounds, and the methods described herein are listed in the Table 5.

TABLE 5

A non-limiting list of infectious diseases.

| Disease | Source of Disease |
|---|---|
| *Acinetobacter* infections | *Acinetobacter baumannii* |
| Actinomycosis | *Actinomyces israelii, Actinomyces gerencseriae* and *Propionibacterium propionicus* |
| African sleeping sickness (African trypanosomiasis) | *Trypanosoma brucei* |
| AIDS (Acquired immunodeficiency syndrome) | HIV (Human immunodeficiency virus) |
| Amebiasis | *Entamoeba histolytica* |
| Anaplasmosis | *Anaplasma* species |
| Angiostrongyliasis | *Angiostrongylus* |
| Anisakiasis | *Anisakis* |
| Anthrax | *Bacillus anthracis* |
| *Arcanobacterium haemolyticum* infection | *Arcanobacterium haemolyticum* |
| Argentine hemorrhagic fever | Junin virus |
| Ascariasis | *Ascaris lumbricoides* |
| Aspergillosis | *Aspergillus* species |
| Astrovirus infection | Astroviridae family |
| Babesiosis | *Babesia* species |
| *Bacillus cereus* infection | *Bacillus cereus* |
| Bacterial pneumonia | multiple bacteria |
| Bacterial vaginosis | List of bacterial vaginosis microbiota |
| *Bacteroides* infection | *Bacteroides* species |
| Balantidiasis | *Balantidium coli* |
| Bartonellosis | *Bartonella* |
| Baylisascaris infection | *Baylisascaris* species |
| BK virus infection | BK virus |

TABLE 5-continued

A non-limiting list of infectious diseases.

| Disease | Source of Disease |
|---|---|
| Black piedra | *Piedraia hortae* |
| Blastocystosis | *Blastocystis* species |
| Blastomycosis | *Blastomyces dermatitidis* |
| Bolivian hemorrhagic fever | Machupo virus |
| Botulism (and Infant botulism) | *Clostridium botulinum*; Note: Botulism is not an infection by *Clostridium botulinum* but caused by the intake of botulinum toxin. |
| Brazilian hemorrhagic fever | Sabia virus |
| Brucellosis | *Brucella* species |
| Bubonic plague | the bacterial family Enterobacteriaceae |
| *Burkholderia* infection | usually *Burkholderia cepacia* and other *Burkholderia* species |
| Buruli ulcer | *Mycobacterium ulcerans* |
| Calicivirus infection (Norovirus and Sapovirus) | Caliciviridae family I |
| Campylobacteriosis | *Campylobacter* species |
| Candidiasis (Moniliasis; Thrush) | usually *Candida albicans* and other *Candida* species |
| Capillariasis | Intestinal disease by *Capillaria philippinensis*, hepatic disease by *Capillaria hepatica* and pulmonary disease by *Capillaria aerophila* |
| Carrion's disease | *Bartonella bacilliformis* |
| Cat-scratch disease | *Bartonella henselae* |
| Cellulitis | usually Group A *Streptococcus* and *Staphylococcus* |
| Chagas Disease (American trypanosomiasis) | *Trypanosoma cruzi* |
| Chancroid | *Haemophilus ducreyi* |
| Chickenpox | Varicella zoster virus (VZV) |
| Chikungunya | Alphavirus |
| Chlamydia | *Chlamydia trachomatis* |
| *Chlamydophila pneumoniae* infection (Taiwan acute respiratory agent or TWAR) | *Chlamydophila pneumoniae* |
| Cholera | *Vibrio cholerae* |
| Chromoblastomycosis | usually *Fonsecaea pedrosoi* |
| Chytridiomycosis | *Batrachochytrium dendrabatidis* |
| Clonorchiasis | *Clonorchis sinensis* |
| *Clostridium difficile* colitis | *Clostridium difficile* |
| Coccidioidomycosis | *Coccidioides immitis* and *Coccidioides posadasii* |
| Colorado tick fever (CTF) | Colorado tick fever virus (CTFV) |
| Common cold (Acute viral rhinopharyngitis; Acute coryza) | usually rhinoviruses and coronaviruses |
| Creutzfeldt-Jakob disease (CJD) | PRNP |
| Crimean-Congo hemorrhagic fever (CCHF) | Crimean-Congo hemorrhagic fever virus |
| Cryptococcosis | *Cryptococcus neoformans* |
| Cryptosporidiosis | *Cryptosporidium* species |
| Cutaneous larva migrans (CLM) | usually *Ancylostoma braziliense*; multiple other parasites |
| Cyclosporiasis | *Cyclospora cayetanensis* |
| Cysticercosis | *Taenia solium* |
| Cytomegalovirus infection | Cytomegalovirus |
| Dengue fever | Dengue viruses (DEN-1, DEN-2, DEN-3 and DEN-4) - Flaviviruses |
| *Desmodesmus* infection | Green algae *Desmodesmus armatus* |
| Dientamoebiasis | *Dientamoeba fragilis* |
| Diphtheria | *Corynebacterium diphtheriae* |
| Diphyllobothriasis | *Diphyllobothrium* |
| Dracunculiasis | *Dracunculus medinensis* |
| Ebola hemorrhagic fever | Ebolavirus (EBOV) |
| Echinococcosis | *Echinococcus* species |
| Ehrlichiosis | *Ehrlichia* species |
| Enterobiasis (Pinworm infection) | *Enterobius vermicularis* |
| *Enterococcus* infection | *Enterococcus* species |
| Enterovirus infection | Enterovirus species |
| Epidemic typhus | *Rickettsia prowazekii* |
| Erythema infectiosum (Fifth disease) | Parvovirus B19 |
| Exanthem subitum (Sixth disease) | Human herpesvirus 6 (HHV-6) and Human herpesvirus 7 (HHV-7) |
| Fasciolasis | *Fasciola hepatica* and *Fasciola gigantica* |
| Fasciolopsiasis | *Fasciolopsis buski* |
| Fatal familial insomnia (FFI) | PRNP |
| Filariasis | Filarioidea superfamily |
| Food poisoning by *Clostridium perfringens* | *Clostridium perfringens* |
| Free-living amebic infection | multiple |
| *Fusobacterium* infection | *Fusobacterium* species |
| Gas gangrene (Clostridial myonecrosis) | usually *Clostridium perfringens*; other *Clostridium* species |

TABLE 5-continued

A non-limiting list of infectious diseases.

| Disease | Source of Disease |
|---|---|
| Geotrichosis | *Geotrichum candidum* |
| Gerstmann-Straussler-Scheinker syndrome (GSS) | PRNP |
| Giardiasis | *Giardia lamblia* |
| Glanders | *Burkholderia mallei* |
| Gnathostomiasis | *Gnathostoma spinigerum* and *Gnathostoma hispidum* |
| Gonorrhea | *Neisseria gonorrhoeae* |
| Granuloma inguinale (Donovanosis) | *Klebsiella granulomatis* |
| Group A streptococcal infection | *Streptococcus pyogenes* |
| Group B streptococcal infection | *Streptococcus agalactiae* |
| *Haemophilus influenzae* infection | *Haemophilus influenzae* |
| Hand, foot and mouth disease (HFMD) | Enteroviruses, mainly Coxsackie A virus and Enterovirus 71 (EV71) |
| Hantavirus Pulmonary Syndrome (HPS) | Sin Nombre virus |
| Heartland virus disease | Heartland virus |
| *Helicobacter pylori* infection | *Helicobacter pylori* |
| Hemolytic-uremic syndrome (HUS) | *Escherichia coli* O157:H7, 0111 and O104:H4 |
| Hemorrhagic fever with renal syndrome (HFRS) | Bunyaviridae family |
| Hepatitis A | Hepatitis A virus |
| Hepatitis B | Hepatitis B virus |
| Hepatitis C | Hepatitis C virus |
| Hepatitis D | Hepatitis D Virus |
| Hepatitis E | Hepatitis E virus |
| Herpes simplex | Herpes simplex virus 1 and 2 (HSV-1 and HSV-2) |
| Histoplasmosis | *Histoplasma capsulatum* |
| Hookworm infection | *Ancylostoma duodenale* and *Necator americanus* |
| Human bocavirus infection | Human bocavirus (HBoV) |
| Human *ewingii* ehrlichiosis | *Ehrlichia ewingii* |
| Human granulocytic anaplasmosis (HGA) | *Anaplasma phagocytophilum* |
| Human metapneumovirus infection | Human metapneumovirus (hMPV) |
| Human monocytic ehrlichiosis | *Ehrlichia chaffeensis* |
| Human papillomavirus (HPV) infection | Human papillomavirus (HPV) |
| Human parainfluenza virus infection | Human parainfluenza viruses (HPIV) |
| Hymenolepiasis | *Hymenolepis nana* and *Hymenolepis diminuta* |
| Epstein-Barr Virus Infectious Mononucleosis (Mono) | Epstein-Barr Virus (EBV) |
| Influenza (flu) | Orthomyxoviridae family |
| Isosporiasis | *Isospora belli* |
| Kawasaki disease | unknown; evidence supports that it is infectious |
| Keratitis | multiple |
| *Kingella kingae* infection | *Kingella kingae* |
| Kuru | PRNP |
| Lassa fever | Lassa virus |
| Legionellosis (Legionnaires' disease) | *Legionella pneumophila* |
| Legionellosis (Pontiac fever) | *Legionella pneumophila* |
| Leishmaniasis | *Leishmania* species |
| Leprosy | *Mycobacterium leprae* and *Mycobacterium lepromatosis* |
| Leptospirosis | *Leptospira* species |
| Listeriosis | *Listeria monocytogenes* |
| Lyme disease (Lyme borreliosis) | *Borrelia burgdorferi*, *Borrelia garinii*, and *Borrelia afzelii* |
| Lymphatic filariasis (Elephantiasis) | *Wuchereria bancrofti* and *Brugia malayi* |
| Lymphocytic choriomeningitis | Lymphocytic choriomeningitis virus (LCMV) |
| Malaria | *Plasmodium* species |
| Marburg hemorrhagic fever (MHF) | Marburg virus |
| Measles | Measles virus |
| Middle East respiratory syndrome (MERS) | Middle East respiratory syndrome coronavirus |
| Melioidosis (Whitmore's disease) | *Burkholderia pseudomallei* |
| Meningitis | multiple |
| Meningococcal disease | *Neisseria meningitidis* |
| Metagonimiasis | usually *Metagonimus yokagawai* |
| Microsporidiosis | Microsporidia phylum |
| Molluscum contagiosum (MC) | Molluscum contagiosum virus (MCV) |
| Monkeypox | Monkeypox virus |
| Mumps | Mumps virus |
| Murine typhus (Endemic typhus) | *Rickettsia typhi* |
| Mycoplasma pneumonia | Mycoplasma pneumoniae |
| Mycetoma (disambiguation) | numerous species of bacteria (*Actinomycetoma*) and fungi (*Eumycetoma*) |
| Myiasis | parasitic dipterous fly larvae |
| Neonatal conjunctivitis (Ophthalmia neonatorum) | most commonly *Chlamydia trachomatis* and *Neisseria gonorrhoeae* |
| (New) Variant Creutzfeldt-Jakob disease (vCJD, nvCJD) | PRNP |
| Nocardiosis | usually *Nocardia asteroides* and other *Nocardia* species |
| Onchocerciasis (River blindness) | *Onchocerca volvulus* |

TABLE 5-continued

A non-limiting list of infectious diseases.

| Disease | Source of Disease |
|---|---|
| Opisthorchiasis | *Opisthorchis viverrini* and *Opisthorchis felineus* |
| Paracoccidioidomycosis (South American blastomycosis) | *Paracoccidioides brasiliensis* |
| Paragonimiasis | usually *Paragonimus westermani* and other *Paragonimus* species |
| Pasteurellosis | *Pasteurella* species |
| Pediculosis capitis (Head lice) | *Pediculus humanus* capitis |
| Pediculosis corporis (Body lice) | *Pediculus humanus* corporis |
| Pediculosis pubis (Pubic lice, Crab lice) | *Phthirus pubis* |
| Pelvic inflammatory disease (PID) | multiple |
| Pertussis (Whooping cough) | *Bordetella pertussis* |
| Plague | *Yersinia pestis* |
| Pneumococcal infection | *Streptococcus pneumoniae* |
| Pneumocystis pneumonia (PCP) | *Pneumocystis jirovecii* |
| Pneumonia | multiple |
| Poliomyelitis | Poliovirus |
| Prevotella infection | *Prevotella* species |
| Primary amoebic meningoencephalitis (PAM) | usually *Naegleria fowleri* |
| Progressive multifocal leukoencephalopathy | JC virus |
| Psittacosis | *Chlamydophila psittaci* |
| Q fever | *Coxiella burnetii* |
| Rabies | Rabies virus |
| Relapsing fever | *Borrelia hermsii, Borrelia recurrentis*, and other *Borrelia* species |
| Respiratory syncytial virus infection | Respiratory syncytial virus (RSV) |
| Rhinosporidiosis | *Rhinosporidium seeberi* |
| Rhinovirus infection | Rhinovirus |
| Rickettsial infection | *Rickettsia* species |
| Rickettsialpox | *Rickettsia akari* |
| Rift Valley fever (RVF) | Rift Valley fever virus |
| Rocky Mountain spotted fever (RMSF) | *Rickettsia rickettsii* |
| Rotavirus infection | Rotavirus |
| Rubella | Rubella virus |
| Salmonellosis | *Salmonella* species |
| SARS (Severe Acute Respiratory Syndrome) | SARS coronavirus |
| Scabies | *Sarcoptes scabiei* |
| Schistosomiasis | *Schistosoma* species |
| Sepsis | multiple |
| Shigellosis (Bacillary dysentery) | *Shigella* species |
| Shingles (Herpes zoster) | Varicella zoster virus (VZV) |
| Smallpox (Variola) | Variola major or Variola minor |
| Sporotrichosis | *Sporothrix schenckii* |
| Staphylococcal food poisoning | *Staphylococcus* species |
| Staphylococcal infection | *Staphylococcus* species |
| Strongyloidiasis | *Strongyloides stercoralis* |
| Subacute sclerosing panencephalitis | Measles virus |
| Syphilis | *Treponema pallidum* |
| Taeniasis | *Taenia* species |
| Tetanus (Lockjaw) | *Clostridium tetani* |
| Tinea barbae (Barber's itch) | usually *Trichophyton* species |
| Tinea capitis (Ringworm of the Scalp) | usually *Trichophyton tonsurans* |
| Tinea corporis (Ringworm of the Body) | usually *Trichophyton* species |
| Tinea cruris (Jock itch) | usually *Epidermophyton floccosum, Trichophyton rubrum,* and *Trichophyton mentagrophytes* |
| Tinea manum (Ringworm of the Hand) | *Trichophyton rubrum* |
| Tinea nigra | usually *Hortaea werneckii* |
| Tinea pedis (Athlete's foot) | usually *Trichophyton* species |
| Tinea unguium (Onychomycosis) | usually *Trichophyton* species |
| Tinea versicolor (Pityriasis versicolor) | *Malassezia* species |
| Toxocariasis (Ocular Larva Migrans (OLM)) | *Toxocara canis* or *Toxocara cati* |
| Toxocariasis (Visceral Larva Migrans (VLM)) | *Toxocara canis* or *Toxocara cati* |
| Trachoma | *Chlamydia trachomatis* |
| Toxoplasmosis | *Toxoplasma gondii* |
| Trichinosis | *Trichinella spiralis* |
| Trichomoniasis | *Trichomonas vaginalis* |
| Trichuriasis (Whipworm infection) | *Trichuris trichiura* |
| Tuberculosis | usually *Mycobacterium tuberculosis* |
| Tularemia | *Francisella tularensis* |
| Typhoid fever | *Salmonella enterica* subsp. *enterica,* serovar typhi |
| Typhus fever | *Rickettsia* |
| *Ureaplasma urealyticum* infection | *Ureaplasma urealyticum* |

TABLE 5-continued

| A non-limiting list of infectious diseases. | |
|---|---|
| Disease | Source of Disease |
| Valley fever | *Coccidioides immitis* or *Coccidioides posadasi*[1] |
| Venezuelan equine encephalitis | Venezuelan equine encephalitis virus |
| Venezuelan hemorrhagic fever | Guanarito virus |
| *Vibrio vulnificus* infection | *Vibrio vulnificus* |
| Vibrio parahaemolyticus enteritis | *Vibrio parahaemolyticus* |
| Viral pneumonia | multiple viruses |
| West Nile Fever | West Nile virus |
| White piedra (Tinea blanca) | *Trichosporon beigelii* |
| *Yersinia pseudotuberculosis* infection | *Yersinia pseudotuberculosis* |
| Yersiniosis | *Yersinia enterocolitica* |
| Yellow fever | Yellow fever virus |

Dose and Administration

The compositions, as described herein, are administered in effective amounts. The effective amount will depend upon the mode of administration, the particular condition being treated and the desired outcome. It will also depend upon, as discussed above, the stage of the condition, the age and physical condition of the subject, the nature of concurrent therapy, if any, and like factors well known to the medical practitioner. For therapeutic applications, it is that amount sufficient to achieve a medically desirable result.

Generally, the dose of the anti-chemorepellant agent of the present invention is from about 0.001 to about 100 mg/kg body weight per day, e.g., about 5 mg/kg body weight per day to about 50 mg/kg per day, e.g., about 5, 10, 15, 20, 25, 30, 35, 40, 45, or 50 mg/kg per day inclusive of all values and ranges therebetween, including endpoints. In one embodiment, the dose is from about 10 mg/kg to about 50 mg/kg per day. In one embodiment, the dose is from about 10 mg/kg to about 40 mg/kg per day. In one embodiment, the dose is from about 10 mg/kg to about 30 mg/kg per day. In one embodiment, the dose is from about 10 mg/kg to about 20 mg/kg per day. In one embodiment, the dose does not exceed about 50 mg per day.

In one embodiment, the dose of the anti-chemorepellant agent is from about 50 mg/kg per week to about 350 mg/kg per week, inclusive of all values and ranges therebetween, including endpoints. In one embodiment, the dose of the anti-chemorepellant agent is about 50 mg/kg per week. In one embodiment, the dose of the anti-chemorepellant agent is about 60 mg/kg per week. In one embodiment, the dose of the anti-chemorepellant agent is about 70 mg/kg per week. In one embodiment, the dose of the anti-chemorepellant agent is about 80 mg/kg per week. In one embodiment, the dose of the anti-chemorepellant agent is about 90 mg/kg per week. In one embodiment, the dose of the anti-chemorepellant agent is about 100 mg/kg per week. In one embodiment, the dose of the anti-chemorepellant agent is about 110 mg/kg per week. In one embodiment, the dose of the anti-chemorepellant agent is about 120 mg/kg per week. In one embodiment, the dose of the anti-chemorepellant agent is about 130 mg/kg per week. In one embodiment, the dose of the anti-chemorepellant agent is about 140 mg/kg per week. In one embodiment, the dose of the anti-chemorepellant agent is about 150 mg/kg per week. In one embodiment, the dose of the anti-chemorepellant agent is about 160 mg/kg per week. In one embodiment, the dose of the anti-chemorepellant agent is about 170 mg/kg per week. In one embodiment, the dose of the anti-chemorepellant agent is about 180 mg/kg per week. In one embodiment, the dose of the anti-chemorepellant agent is about 190 mg/kg per week. In one embodiment, the dose of the anti-chemorepellant agent is about 200 mg/kg per week. In one embodiment, the dose of the anti-chemorepellant agent is about 210 mg/kg per week. In one embodiment, the dose of the anti-chemorepellant agent is about 220 mg/kg per week. In one embodiment, the dose of the anti-chemorepellant agent is about 230 mg/kg per week. In one embodiment, the dose of the anti-chemorepellant agent is about 240 mg/kg per week. In one embodiment, the dose of the anti-chemorepellant agent is about 250 mg/kg per week. In one embodiment, the dose of the anti-chemorepellant agent is about 260 mg/kg per week. In one embodiment, the dose of the anti-chemorepellant agent is about 270 mg/kg per week. In one embodiment, the dose of the anti-chemorepellant agent is about 280 mg/kg per week. In one embodiment, the dose of the anti-chemorepellant agent is about 290 mg/kg per week. In one embodiment, the dose of the anti-chemorepellant agent is about 300 mg/kg per week. In one embodiment, the dose of the anti-chemorepellant agent is about 310 mg/kg per week. In one embodiment, the dose of the anti-chemorepellant agent is about 320 mg/kg per week. In one embodiment, the dose of the anti-chemorepellant agent is about 330 mg/kg per week. In one embodiment, the dose of the anti-chemorepellant agent is about 340 mg/kg per week. In one embodiment, the dose of the anti-chemorepellant agent is about 350 mg/kg per week.

In one aspect of the invention, administration of the anti-chemorepellant agent is pulsatile. In one embodiment, an amount of anti-chemorepellant agent is administered every 1 hour to every 24 hours, for example every 1 hour, 2 hours, 3 hours, 4 hours, 5 hours, 6 hours, 7 hours, 8 hours, 9 hours, 10 hours, 11 hours, 12 hours, 13 hours, 14 hours 15 hours, 16 hours, 17 hours, 18 hours, 19 hours, 20 hours, 21 hours, 22 hours, 23 hours, or 24 hours. In one embodiment, an amount of anti-chemorepellant agent is administered every 1 day, 2 days, 3 days, 4 days, 5 days, 6 days, 7 days, 8 days, 9 days, or 10 days.

In one aspect of the invention, doses of the anti-chemorepellant agent are administered in a pulsatile manner for a period of time sufficient to have an anti-chemorepellant effect (e.g., to attenuate the chemorepellant effect of the pathogen or the pathogen-infected cell). In one embodiment, the period of time is between about 1 day and about 10 days. For example, the period of time may be 1 day, 2 days, 3 days, 4 days, 5 days, 6 days, 7 days, 8 days, 9 days, or 10 days. In some embodiments, the fusion protein is administered after the anti-chemorepellant effect has occurred, e.g., one or more days after the anti-chemorepellant agent has been administered. In some embodiments, administration of the chemorepellant agent is continued while the fusion protein is being administered.

A variety of administration routes are available. The methods of the invention, generally speaking, may be practiced using any mode of administration that is medically acceptable, meaning any mode that produces effective levels of the active compounds without causing clinically unacceptable adverse effects.

Modes of administration include oral, rectal, topical, nasal, intradermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule. When peptides are used therapeutically, in certain embodiments a desirable route of administration is by pulmonary aerosol. Techniques for preparing aerosol delivery systems containing peptides are well known to those of skill in the art. Generally, such systems should utilize components which will not significantly impair the biological properties of the antibodies, such as the paratope binding capacity (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing antibody or peptide aerosols without resort to undue experimentation.

Compositions suitable for oral administration may be presented as discrete units, such as capsules, tablets, lozenges, each containing a predetermined amount of the active agent(s). Other compositions include suspensions in aqueous liquids or non-aqueous liquids such as a syrup, elixir or an emulsion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed 25 oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In one embodiment, the anti-chemorepellant agent is administered parenterally. In one embodiment, the anti-chemorepellant agent is administered via microcatheter into a blood vessel proximal to pathogen or pathogen-infected cells. In one embodiment, the anti-chemorepellant agent is administered via microcatheter into a blood vessel within the tissue infected by pathogen. In one embodiment, the anti-chemorepellant agent is administered subcutaneously. In one embodiment, the anti-chemorepellant agent is administered intradermally.

Other delivery systems can include time-release, delayed release or sustained release delivery systems. Such systems can avoid repeated administrations of the anti-chemorepellant agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like.

In one embodiment, the anti-chemorepellant agent is administered in a time-release, delayed release or sustained release delivery system. In one embodiment, the time-release, delayed release or sustained release delivery system comprising the anti-chemorepellant agent is inserted directly into the pathogen-infected cells. In one embodiment, the time-release, delayed release or sustained release delivery system comprising the anti-chemorepellant agent is implanted in the patient infected with the pathogen. Additional implantable formulations are described, for example, in U.S. Patent App. Pub. No. 2008/0300165, which is incorporated herein by reference in its entirety.

In addition, important embodiments of the invention include pump-based hardware delivery systems, some of which are adapted for implantation. Such implantable pumps include controlled-release microchips. An exemplary controlled-release microchip is described in Santini, J T Jr. et al., Nature, 1999, 397:335-338, the contents of which are expressly incorporated herein by reference.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Dosages, methods, and means of administration of anti-pathogen agents are well-known in the art and can be determined by a skilled clinician.

Pharmaceutical Compositions

In one aspect, this invention relates to a pharmaceutical composition comprising a fusion protein as described herein and an anti-chemorepellant agent. In one embodiment, the composition further comprises antigen-presenting cells. In one embodiment, the antigen-presenting cells are dendritic cells. In one embodiment, the antigen-presenting cells are derived from the patient to be treated. In one embodiment, the antigen-presenting cells express CXCR4 and/or CXCR7 on the cell surface.

In one embodiment, the composition further comprises an anti-pathogen agent.

In one embodiment, the composition comprises an effective amount of the fusion protein to activate the antigen-presenting cells. In one embodiment, the composition comprises an effective amount of the anti-chemorepellant agent to reduce the chemorepellant effect of the pathogen. In one embodiment, the composition comprises an effective amount of the antigen presenting cells to result in activation of T cells against the pathogen.

In one embodiment, the pharmaceutical composition is formulated for injection.

In one embodiment, the composition comprises a pharmaceutically acceptable excipient. Acceptable excipients are non-toxic, aid administration, and do not adversely affect the therapeutic benefit of the claimed compounds. Such excipient may be any solid, liquid, semi-solid or gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutical excipients and their formulations are described in Remington's Pharmaceutical Sciences, edited by E. W. Martin (Mack Publishing Company, 22nd ed., 2013).

In order to ensure that the dendritic cells and fusion protein interact once administered to a patient, the cells and protein may be combined prior to administration. In one embodiment, the cells and protein are combined immediately (e.g., seconds to one or two hours) prior to administration to the patient.

Without being bound by theory, it is believed that combination of the antigen-presenting cells and the anti-chemorepellant agent prior to administration to the patient will allow binding of the anti-chemorepellant agent to cell surface receptors (e.g., CXCR4 or CXCR7), thereby allowing the cells to overcome the chemorepellant effect of the pathogen. In contrast, it is contemplated that the systemic delivery of an anti-chemorepellant agent results in indiscriminate binding of that agent to CXCR4 and/or CXCR7 receptors throughout the body.

Kit of Parts

In one aspect, this invention relates to a kit of parts for treatment of a disease, the kit comprising a fusion protein and an anti-chemorepellant agent. In one embodiment, the composition further comprises an anti-pathogen agent.

In one embodiment is provided a kit of parts for treatment of an infectious disease or a pathogen in a patient, the kit comprising a therapeutically effective amount of an anti-chemorepellant agent and a fusion protein comprising a pathogen binding component and a stress protein component, wherein the pathogen binding component recognizes an antigen expressed by the pathogen or a pathogen-infected cell.

In one embodiment, the anti-chemorepellant agent is any of the agents disclosed previously, e.g., selected from the group consisting of AMD3100 or a derivative thereof, AMD11070 (also called AMD070), AMD12118, AMD11814, AMD13073, FAMD3465, C131, BKT140, CTCE-9908, KRH-2731, TC14012, KRH-3955, BMS-936564/MDX-1338, LY2510924, GSK812397, KRH-1636, T-20, T-22, T-140, TE-14011, T-14012, TN14003, TAK-779, AK602, SCH-351125, tannic acid, NSC 651016, thalidomide, GF 109230X, an antibody that interferes with dimerization of a chemorepellant chemokine, and an antibody that interferes with dimerization of a receptor for a chemorepellant chemokine. In one embodiment, the anti-chemorepellant agent is AMD3100 or a derivative thereof. In one embodiment, the anti-chemorepellant agent is AMD3100.

In one embodiment, the stress protein is HSP70 or an immune activating fragment and/or modified sequence thereof. In one embodiment, the HSP70 or the immune activating fragment or modified sequence thereof is from *Mycobacterium tuberculosis.*

In one embodiment, the tumor binding component is a single chain antibody, a variable domain, or a Fab domain.

In one embodiment, the fusion protein and/or the anti-chemorepellant agent are formulated for injection.

In one embodiment, the fusion protein and the anti-chemorepellant agent are in the same formulation. In one embodiment, the anti-pathogen agent is in the same formulation as the fusion protein and/or the anti-chemorepellant agent. In one embodiment, one or more of the anti-chemorepellant agent, fusion protein, and/or anti-pathogen agent are in separate formulation(s).

In one embodiment, the kit further comprises instructions for treating the pathogen. In one embodiment, the kit of parts comprises instructions in a readable medium for dosing and/or administration of the anti-chemorepellant agent and the fusion protein.

The term "readable medium" as used herein refers to a representation of data that can be read, for example, by a human or by a machine. Non-limiting examples of human-readable formats include pamphlets, inserts, or other written forms. Non-limiting examples of machine-readable formats include any mechanism that provides (i.e., stores and/or transmits) information in a form readable by a machine (e.g., a computer, tablet, and/or smartphone). For example, a machine-readable medium includes read-only memory (ROM); random access memory (RAM); magnetic disk storage media; optical storage media; and flash memory devices. In one embodiment, the machine-readable medium is a CD-ROM. In one embodiment, the machine-readable medium is a USB drive. In one embodiment, the machine-readable medium is a Quick Response Code (QR Code) or other matrix barcode.

Examples

Example 1. Fusion Protein Targeting HBV

Rationale: Current antiviral treatment of chronic hepatitis B (HBV) results in sustainable host viral control in only 25% of infected individuals. Alternative therapeutic vaccine approaches focused on boosting T cell responses in these patients to achieve viral clearance have proven challenging due to the exhausted and suppressed state of HBV-specific T cells. While a dendritic cell vaccine approach shows promise in reversing T cell exhaustion or suppression, clinical use of such vaccines will be individualized, complex and expensive. In this context an alternative approach that uses a scalable recombinant protein to induce the same type of effects as dendritic cell vaccines would offer a solution more amenable for wide application. Such an approach could be built on the use of *Mycobacterium tuberculosis* heat shock protein 70 (MtbHSP70), which can target dendritic cells, promote both uptake and class I and class II processing of pathogen antigens, and stimulate release of immunostimulatory cytokines that activate and enhance maturation of these dendritic cells. These advantages to using MtbHSP70 with hepatitis B vaccines have been demonstrated in preclinical vaccines that incorporate specific hepatitis B antigens or epitopes for standard vaccination. The approach fuses MtbHSP70 to a single chain variable fragment (scFv) capable of high-affinity binding to a HBV surface antigen (HBsAg). The fusion protein binds to virus via the scFv, while the MtbHSP70 portion both stimulates dendritic cells and induces virus uptake, resulting in cross-presentation of viral antigens to T cells and B cells by activated dendritic cells. The fusion protein effectively induces an in situ immune response in both the blood and liver, where virus may be circulating or replicating, respectively.

Hypothesis:

A scFv-MtbHSP70 fusion protein targeting HBsAg on circulating/liver HBV virions can induce uptake and cross-presentation of multiple HBV antigens by dendritic cells leading to significant multivalent, viral-specific T cell and B cell responses in a transgenic mouse model of chronic HBV infection.

Innovation:

The central innovation of this project is to induce the immunologic responses found in dendritic cell vaccination by using a scalable therapeutic protein that can facilitate "in vivo dendritic cell vaccination." This novel immunotherapy approach for overcoming immune tolerance or exhaustion in HBV infection could contribute to strategies for eliciting sustained immunological control of chronic HBV, either alone or in combination with standard of care antiviral therapies, and offer hope of an effective curative therapy.

Study Design:

A scFv-MtbHSP70 fusion protein targeting HBsAg is constructed and characterized for research use. Initial in vitro studies demonstrate functional integrity of both the scFv (binding affinity to HBsAg) and MtbHSP70 (ATPase activity) components. The immune effects of the therapeutic protein is tested in HBV transgenic mice. Mice treated with the fusion protein or with MtbHSP70 alone and PBS as negative controls are evaluated for cellular (IFNγ production by antigen-stimulated splenocytes) and humoral (serum IgG) responses to both HBSAg antigen and HBV core protein. Liver histology, liver HBV DNA content, and serum alanine aminotransferase levels are assessed as indicators of antiviral cytotoxic responses. In addition, the immune system's response to the targeted immunotherapy is characterized using cytometry by time-of-flight mass spectrometry (CyTOF) for simultaneous measurement of >35 immune parameters.

Expected Results:

Results from this project demonstrating activation of immune responses to HBV in the transgenic mouse model will be used to develop a preclinical therapeutic candidate for clinical evaluation in chronic HBV patients.

The foregoing is illustrative of the present invention, and is not to be construed as limiting thereof. The invention is defined by the following claims, with equivalents of the claims to be included therein.

What is claimed is:

1. A method for treating a tumor resulting from a viral infection in a patient wherein a virus from the viral infection induces or expresses chemorepellant properties, the method comprising:

a) administering to the patient an effective amount of a fusion protein comprising a virus binding component and a stress protein component, wherein said virus binding component binds to the virus and said stress protein component activates antigen-presenting cells; and b) concurrently administering to said patient an effective amount of AMD3100;

wherein the combination of the fusion protein and AMD3100 treats the tumor resulting from a viral infection, wherein the viral infection is human papillomavirus (HPV) infection.

2. The method of claim 1, wherein the stress protein is HSP70 or an immune activating fragment thereof.

3. The method of claim 2, wherein the HSP70 or the immune activating fragment thereof is from *Mycobacterium tuberculosis*.

4. The method of claim 1, wherein the virus binding component is an antibody or a fragment thereof, a single chain antibody, a variable domain, or a Fab domain.

5. A pharmaceutical composition for treating a tumor resulting from a viral infection comprising:

(a) a fusion protein comprising a virus binding component wherein the virus binding component recognizes an antigen expressed by the tumor resulting from the viral infection, and a stress protein component; and (b) AMD3100, wherein the viral infection is human papillomavirus (HPV) infection.

6. The pharmaceutical composition of claim 5, further comprising antigen-presenting cells.

7. The pharmaceutical composition of claim 6, wherein the antigen-presenting cells are dendritic cells.

8. The pharmaceutical composition of claim 5, wherein the stress protein is HSP70 or an immune activating fragment thereof.

9. The pharmaceutical composition of claim 8, wherein the HSP70 or the immune activating fragment thereof is from *Mycobacterium tuberculosis*.

10. The pharmaceutical composition of claim 5, wherein the virus binding component is an antibody or a fragment thereof, a single chain antibody, a variable domain, or a Fab domain.

11. A kit of parts for treatment of a tumor resulting from a viral infection in a patient, the kit comprising a therapeutically effective amount of AMD3100 and a fusion protein comprising a virus binding component and a stress protein component, wherein the virus binding component recognizes an antigen expressed by a tumor resulting from a viral infection, wherein the viral infection is human papillomavirus (HPV) infection.

12. The kit of parts of claim 11, wherein the stress protein is HSP70 or an immune activating fragment thereof.

13. The kit of parts of claim 12, wherein the HSP70 or the immune activating fragment thereof is from *Mycobacterium tuberculosis*.

14. The kit of parts of claim 11, wherein the virus binding component is an antibody or a fragment thereof, a single chain antibody, a variable domain, or a Fab domain.

* * * * *

UNITED STATES PATENT AND TRADEMARK OFFICE
CERTIFICATE OF CORRECTION

| | | |
|---|---|---|
| PATENT NO. | : 11,453,706 B2 | |
| APPLICATION NO. | : 16/331847 | |
| DATED | : September 27, 2022 | |
| INVENTOR(S) | : Mark C. Poznansky and Jeffrey A. Gelfand | |

It is certified that error appears in the above-identified patent and that said Letters Patent is hereby corrected as shown below:

In the Claims

In Column 32, Line 24 (approx.), in Claim 5, delete "component" and insert -- component, --

Signed and Sealed this
Tenth Day of January, 2023

Katherine Kelly Vidal
*Director of the United States Patent and Trademark Office*